(12) United States Patent
Naguib et al.

(10) Patent No.: US 7,989,493 B2
(45) Date of Patent: Aug. 2, 2011

(54) NATURAL VITAMIN E COMPOSITIONS WITH SUPERIOR ANTIOXIDANT POTENCY

(75) Inventors: Yousry M. A. Naguib, Arcadia, CA (US); Ronald G. Udell, Beverly Hills, CA (US); Richard A. Passwater, Jr., Long Beach, CA (US); Melvin Lee Rich, Melville, NY (US)

(73) Assignee: Soft Gel Technologies, Inc., Los Angeles, CA (US)

( * ) Notice: Subject to any disclaimer, the term of this patent is extended or adjusted under 35 U.S.C. 154(b) by 0 days.

(21) Appl. No.: 12/267,914

(22) Filed: Nov. 10, 2008

(65) Prior Publication Data

US 2009/0156664 A1 Jun. 18, 2009

Related U.S. Application Data

(63) Continuation of application No. 11/311,533, filed on Dec. 19, 2005, now Pat. No. 7,449,491, which is a continuation of application No. 10/321,318, filed on Dec. 17, 2002, now Pat. No. 7,329,688.

(51) Int. Cl.
*A61K 31/355* (2006.01)
(52) U.S. Cl. ....................................................... 514/458
(58) Field of Classification Search .................... 514/458
See application file for complete search history.

(56) References Cited

U.S. PATENT DOCUMENTS

| | | |
|---|---|---|
| 2,940,900 A | 6/1960 | Benton, Jr. et al. |
| 3,102,078 A | 8/1963 | Robeson |
| 3,212,901 A | 10/1965 | Robeson |
| 3,564,097 A | 2/1971 | Magid |
| 4,364,945 A | 12/1982 | Whittle |
| 4,551,332 A | 11/1985 | Stillman |
| 4,612,194 A | 9/1986 | Ismail |
| 4,711,894 A | 12/1987 | Wenzel et al. |
| 5,102,659 A | 4/1992 | Hudson |
| 5,114,957 A | 5/1992 | Hendler et al. |
| 5,179,122 A | 1/1993 | Greene et al. |
| 5,348,974 A | 9/1994 | Wright et al. |
| 5,352,696 A | 10/1994 | Kim |
| 5,376,361 A | 12/1994 | Perricone |
| 5,387,579 A | 2/1995 | Meybeck et al. |
| 5,545,398 A | 8/1996 | Perricone |
| 5,591,772 A | 1/1997 | Lane et al. |
| 5,919,818 A | 7/1999 | Lane et al. |
| 5,948,769 A | 9/1999 | Ismail |
| 5,985,344 A | 11/1999 | Cherukuri et al. |
| 5,997,892 A | 12/1999 | Camp |
| 6,048,891 A | 4/2000 | Wechter |
| 6,239,171 B1 | 5/2001 | Lane et al. |
| 6,303,586 B1 | 10/2001 | McPeak et al. |
| 6,358,997 B1 | 3/2002 | Clark et al. |
| 6,716,451 B1 | 4/2004 | Udell et al. |
| 7,012,092 B2 | 3/2006 | Rich et al. |
| 7,015,245 B2 | 3/2006 | Rich et al. |
| 7,329,688 B2 | 2/2008 | Naguib et al. |
| 7,449,491 B2 | 11/2008 | Naguib et al. |
| 2001/0046548 A1 | 11/2001 | Berry et al. |
| 2004/0106674 A1 | 6/2004 | Rich et al. |
| 2004/0116512 A1 | 6/2004 | Naguib et al. |
| 2006/0105034 A1 | 5/2006 | Rich et al. |
| 2006/0106093 A1 | 5/2006 | Rich et al. |

FOREIGN PATENT DOCUMENTS

| | | |
|---|---|---|
| JP | 07-163379 | 6/1995 |
| WO | WO 96/19218 | 6/1996 |
| WO | WO 2004/056348 | 7/2004 |

OTHER PUBLICATIONS

Brigelius-Flohe et al., "Vitamin E: function and metabolism," *The FASEB Journal*, Jul. 1999, vol. 13, pp. 1145-1155.
International Search Report dated Jul. 5, 2004, PCT/US03/40398 (WO 04/056348), 3 pages.
Blumberg, "Unraveling the Conflicting Studies on Vitamin E and Heart Disease," May 2002, http://lpi.oregonstate.edu/ss02/blumberg.html, 3 pages.
Burton et al., "Human plasma and tissue α-tocopherol concentrations in response to supplementaion with deuterated natural and synthetic vitamin E," *American Journal of Clinical Nutrition*, 1998, vol. 67, pp. 669-684.
Fontenot, "Nutrition Forum: Can Vitamin E Prevent Heart Disease?," http://findarticles.com/p/articles/mi_m0GCU/is_4_16/ai_55182666/print, 1999, 3 pages.
Kamat et al., "Tocotrienols from palm oil as effective inhibitors of protein oxidation and lipid peroxidation in rat liver microsomes," *Molecular and Cellular Biochemistry*, vol. 170, pp. 131-138, 1997.
Ng, et al., "Effects of Tocotrienol-Rich and Tocopherol-Rich Fractions from Palm Oil on Serum Lipids and Platelet Aggregation in the Rat," 1990, Asean Food Journal, Asean Food Handling Bureau, Kuala Lumpur, MY, pp. 165-169, XP001038596, Issn: 0127-7324.
Traber et al., http://lpi.oregonstate.edu/ss02/ blumberg.html, The Alpha-tocopherol Transfer Protein and Vitamin E Adequacy, May 2001, pp. 1-4.
womenfitness.net, "Comparison of Natural and Synthetic Vitamin E," Nov. 1, 2007, pp. 1-2.

(Continued)

*Primary Examiner* — San-Ming Hui
(74) *Attorney, Agent, or Firm* — Dorsey & Whitney LLP

(57) ABSTRACT

Compositions for increased antioxidant potency of natural vitamin E(d-alpha-tocopherol), comprising alpha-, beta-, delta-, and gamma-forms of tocopherols and tocotrienols are disclosed. All of these compositions provide 400 International Units (IU), based on one mg of d-alpha-tocopherol provides 1.49 IU. These compositions showed antioxidant activities superior to natural d-alpha-tocopherol. These compositions are designed to provide protection of the cell membrane lipid layer, and protection against heart disease, cancer, and eye disease.

5 Claims, No Drawings

OTHER PUBLICATIONS

Notice of Allowance and Fee(s) Due dated Sep. 17, 2007, U.S. Appl. No. 10/321,318, 6 pages.
Amendment & Response dated Aug. 31, 2007, U.S. Appl. No. 10/321,318, 6 pages.
Terminal Under Disclaimers (two) dated Aug. 31, 2007 U.S. Appl. No. 10/321,318, 4 pages.
Non-Final Office Action dated May 31, 2007, U.S. Appl. No. 10/321,318, 5 pages.
Amendment & Response dated Mar. 19, 2007, U.S. Appl. No. 10/321,318, 9 pages.
Non-Final Office Action dated Oct. 19, 2006, U.S. Appl. No. 10/321,318, 8 pages.
Request Under Continued Examination dated Aug. 17, 2006, U.S. Appl. No. 10/321,318, 1 page.
Response dated Aug. 17, 2006, U.S. Appl. No. 10/321,318, 9 pages.
Notice of Appeal to the Board of Patent Appeals and Interferences dated Apr. 17, 2006, U.S. Appl. No. 10/321,318, 2 pages.
Amendment and Response dated Dec. 19, 2005, U.S. Appl. No. 10/321,318, 8 pages.
Final Office Action dated Oct. 17, 2005, U.S. Appl. No. 10/321,318, 8 pages.
Amendment and Response dated Aug. 2, 2005, U.S. Appl. No. 10/321,318, 8 pages.
Terminal Under Disclaimer dated Aug. 2, 2005, U.S. Appl. No. 10/321,318, 2 pages.
Non-Final Office Action dated Jul. 1, 2005, U.S. Appl. No. 10/321,318, 6 pages.
Notice of Allowance and Fee(s) Due dated Aug. 21, 2008, U.S. Appl. No. 11/311,533, 7 pages.
Amendment and Response dated Jun. 20, 2008, U.S. Appl. No. 11/311,533, 4 pages.
Terminal Under Disclaimer dated Jun. 20, 2008, U.S. Appl. No. 11/311,533, 2 pages.
Non-Final Office Action dated May 19, 2008, U.S. Appl. No. 11/311,533, 5 pages.
Amendment and Response dated Feb. 18, 2008, U.S. Appl. No. 11/311,533, 4 pages.
Terminal Under Disclaimer dated Feb. 18, 2008, U.S. Appl. No. 11/311,533, 6 pages.
Non-Final Office Action dated Nov. 6, 2007, U.S. Appl. No. 11/311,533, 6 pages.

NATURAL VITAMIN E COMPOSITIONS WITH SUPERIOR ANTIOXIDANT POTENCY

CROSS-REFERENCE TO RELATED APPLICATION(S)

This application is a continuation of U.S. patent application Ser. No. 11/311,533, filed Dec. 19, 2005, entitled "Natural Vitamin E Compositions with Superior Antioxidant Potency" which is a Continuation of application Ser. No. 10/321,318, filed Dec. 17, 2002, entitled "Natural Vitamin E Compositions with Superior Antioxidant Potency", subject matter of which are incorporated herewith by reference.

FIELD OF THE INVENTION

This invention relates to a novel composition comprising natural d-alpha-tocopherol, mixed natural tocopherols (alpha-tocopherol, beta-tocopherol, gamma-tocopherol, delta-tocopherol), and tocotrienols (alpha-tocotrienol, beta-tocotrienol, gamma-tocotrienol, delta-tocotrienol) having a synergistic antioxidant activity more potent than the antioxidant activity of natural d-alpha-tocopherol.

BACKGROUND OF THE INVENTION

Vitamin E is a generic name for a family of four compounds (forms) of tocopherols and four compounds of tocotrienols. All eight compounds have a chromanol ring structure and a side chain. There are four tocopherol forms (alpha, beta, delta, and gamma) with a fully saturated side chain; and four tocotrienol forms (alpha, beta, delta, and gamma) having unsaturated side chains with double bonds at the 3', 7', and 11' positions in the side chain. The four compounds of both tocopherols and tocotrienols differ from each other in the number and position of methyl groups in the aromatic chromanol ring. Alpha-isomers have all three methyl groups in the chromanol ring. Beta and gamma have tow methyl groups but at different positions in the aromatic chromanol ring. Delta has only one methyl group in the chromanol ring.

Recently, the term natural vitamin E has become synonymous with only alpha-tocopherol. The vitamin E compounds are light yellow oils at room temperature and are fairly stable to heat and acid and degrade with alkaline conditions, and when exposed to ultra violet light, and when exposed to the oxygen air.

Foods that are rich in vitamin E include dark green vegetables, eggs, fish, nuts, soy beans, vegetable oils, wheat germ, and whole-grain products. However, foods are commonly depleted of vitamin E due to processing, refining and storage. After absorption in the intestine, vitamin E is transported to the blood circulation by lipoproteins. As a fat-soluble vitamin, vitamin E is amenable for entry and storage in cell membranes.

The health beneficial effects of vitamin E are, in part, due to their antioxidant property. Vitamin E is the primary defense against cell membrane and DNA damage and protects LDL and other lipid-rich tissues against oxidation. Vitamin E prevents the oxidation of unsaturated and polyunsaturated fatty acids.

Tocotrienols, due to their unsaturated side chains, provide much stronger antioxidant effects and protect against oxidation of "bad" cholesterol, LDL, which, if oxidized, leads to buildup of plaques in arteries and increased risk of heart attack or stroke. The beneficial effects of tocotrienols also include cholesterol lowering, tumor suppressive effect, and inhibition of blood platelet aggregation.

Reactive oxygen species are of great interest in medicine because of the overwhelming evidence relating them to aging and various disease processes such as atherosclerosis, brain dysfunction, birth defects, cataracts, cancer, immune system decline, rheumatoid arthritis, and inflammatory bowel diseases. A complex antioxidant network, such as vitamin E, is effective to counteract reactive oxygen species that are detrimental to human life.

Research studies have indicated that major diseases that afflict humankind worldwide may be preventable by the intake of nutritional supplements, such as antioxidants. The term "antioxidant" nutritional agent has been applied to a number of specific nutrients; including vitamin E. Antioxidants use therefore has gained popularity to prevent disease and to promote health. These compounds are readily available, and non-toxic.

Antioxidants function by neutralizing the harmful effects of free radicals. Free radicals are unstable, highly reactive molecules that circulate in the bloodstream. Some of these free radicals result from lifestyle factors like environmental stress and strenuous exercise, as well as natural processes like aging. To become chemically stable, free radicals take electrons from other molecules in the body, a process that causes cell damage (oxidative damage). Antioxidants prevent oxidative damage by donating electrons to free radicals. As a fat-soluble vitamin, Vitamin E is amenable for entry and storage in cell membranes to react with free-radical molecules and reduce the damage they cause.

The normal metabolic processes release some free radicals that might cause oxidative damage to our body, but our body repairs most of the oxidative damage caused by these free radicals. However, if we flood our bloodstream with an unusually large number of free radicals, typically by smoking or by eating a high-fat diet, over time, oxidative damage can overwhelm the body's repair mechanisms, setting us up for degenerative diseases. Antioxidants protect cells from the damage caused by free radicals.

Insufficient vitamin E results in free radical mediated lipid peroxidation of membranes and their destruction. Vitamin E protects the skeletal muscles, nervous system, and retina of the eye from oxidation. Vitamin E is essential for normal immune function. Vitamin E mitigates the prostaglandin driven severity of inflammation, PMS and circulatory disorders. Vitamin E may reduce the toxicity of metals and protect against free radical promoting environmental pollutants such as ozone, oxides of nitrogen, drugs, alcohol and smoking. Aging is essentially oxidative deterioration of tissues. Since vitamin E can prevent or slow down reactions of such oxidative damage, vitamin E may slow the aging process. The importance of antioxidants stems from the number of diseases where they play a preventive role, such as heart disease, cancer, and eye disease.

Epidemiological studies suggest that low blood levels of vitamin E are associated with increased risk of development of degenerative diseases including coronary heart disease, Alzheimer's disease, cataracts, and certain types of cancer. Two epidemiological studies of more than 12,000 adults conducted at Harvard University found a 40 percent decrease in heart disease risk in subjects taking at least 100 I.U. of vitamin E daily. However, people taking a higher dose of vitamin E supplements with only alpha-tocopherol may not be realizing full benefit. This is further substantiated by a recent study indicating that gamma-tocopherol traps mutagenic electrophiles such as nitric oxide and complements alpha tocopherol.

Oral doses of vitamin E ranging from 50 to 400 International Units (I.U.) per day did not show any adverse effects in double-blind clinical studies. The recommended daily amount (RDA) is 8 to 10 mg per day for healthy adults. In the U.S., 400 I.U. soft gelatin capsules are the most popular dosage from vitamin E. To achieve the potency of a 400 I.U. capsule, a person needs to consume 450 g of sunflower seeds, 2.2 kg of wheat germ or 1.9 liters of corn oil totaling 8,000 calories daily.

Fat soluble vitamins, like vitamin E, are found in foods associated with lipids and are absorbed from the intestine with dietary fats. Therefore, vitamin E intake is recommended with a meal and normally 20 to 40 percent of the ingested vitamin E is absorbed. Multiple doses instead of a single dose of vitamin E taken daily with a meal seem to indicate increased absorption and utility in the body. In fact, a combination of tocopherols, tocotrienols and phospholipids emulsifier have been shown to be effective carrier of molecules for improved absorption. In cardiovascular clinical studies, 50 mg/day vitamin E was used for a period ranging from 1 to 8.2 years without any adverse effects. Vitamin E is the least toxic among the fat soluble vitamins. No evidence of detrimental effects of vitamin E is observed even at daily doses of 100 to 500 mg. Human studies at daily 240 mg doses of tocotrienols for 18 to 24 months did not indicate any adverse effects. Further animal studies show safety of tocotrienols up to 12,000 mg/day.

Recent research studies have shown that a balanced intake of a full spectrum of vitamin E (gamma-, alpha-, beta- and delta-tocopherols) is the best way to overall health benefits. Research also showed tocotrienols from rice bran to be superior in reducing the atherosclerosis Lesion size in mice, thereby providing a unique approach to promoting cardiovascular health.

Gamma-tocopherol, the principle form of vitamin E in the diet, has been scientifically proven to enhance the health benefits of alpha-tocopherol, and is superior in promoting cardiovascular, brain, and immune health.

Gamma-tocopherol was also found to be superior to alpha-tocopherol in protecting cells against peroxynitrite, a harmful chemical that alters DNA and causes cancer. The study suggested that vitamin E supplement should contain at least 20% gamma-tocopherol.

A nested case-control study involving men who developed prostate cancer and matched control subjects showed that men with high blood levels of gamma tocopherol had a significant reduction in the risk of developing prostate cancer. The study also found a significant protective association for high levels of selenium and alpha tocopherol only in men with high gamma-tocopherol concentration.

In a recent study, gamma-tocopherol and alpha-carotene were found to be significantly lower in plasma of coronary heart disease patients compared to healthy people, suggesting that the plasma level of gamma-tocopherol might represent a marker of atherosclerosis in humans.

In an in vivo study, gamma-tocopherol was found to enhance the bio-potency of alpha-tocopherol. Gamma-Tocopherol induced a marked increase in alpha-tocopherol concentrations in the serum and in nerve tissues, heart, liver, and muscle in rats fed diets containing both gamma-tocopherol and alpha-tocopherol more than those fed a diet containing alpha-tocopherol alone.

In an animal study involving spontaneously hypertensive rats, gamma-Tocotrienol was also found to prevent development of increased blood pressure, to reduce lipid peroxidation in plasma and blood vessels, and to enhance total antioxidant status including superoxide dismutase activity. A recent study also showed that supplementation with 100 mg/day tocotrienol-rich fraction of rice bran for a month resulted in a significant reduction in total cholesterol, LDL-cholesterol and triglycerides.

These studies demonstrated that a composition comprising a full spectrum of all forms of tocopherols and tocotrienols will provide greater health benefits of vitamin E than the only form alpha-tocopherol. New compositions of vitamin E comprising all forms of vitamin E were formulated to meet certain criteria: the desired 400 I.U., higher antioxidant potency than alpha-tocopherol, and comparable cost to the commercially marketed natural vitamin E.

Only recently have reliable analytical methods became available to quantitatively measure the total antioxidant capacities, such as oxygen radical absorbance capacity (ORAC) assay, to evaluate the potency of antioxidant formulations. The ORAC method utilizes a peroxyl radical generator and beta-phycoerythrin protein as an indicator of oxidation by measuring the fluorescence of the protein. The ORAC values are expressed as micromoles of Trolox (6-hydroxy-2, 5,7,8-tetramethylchroman-2-onecarboxylic acid) equivalents per liter of the sample and Trolox shows total inhibition of the peroxyl radical action.

The ORAC assay is a widely accepted method in the world for identifying the antioxidant potential in a sample. The samples can be a pure compound, blood plasma, various tissues and foods such as fruits, vegetables, or dietary supplements. The total antioxidant capacity is reflected from various anti oxidants present in the sample and their interactions. The advantage of this assay is that it helps quantify the antioxidant potential value of a sample compared to other commercial samples.

Several other methods have been developed to measure the total antioxidant capacity of a sample. However, the peroxyl or hydroxyl radicals used in the ORAC assay as pro-oxidants make it different and unique from the other assays that involve oxidants that are not necessarily pro-oxidants. Further, substantial deficiencies of other methods have overcome in the ORAC assay. For example, the ORAC assay was compared to other assays and the ORAC assay seems to provide a better correlation to the antioxidant capacity. Therefore, the ORAC assay method provides a valuable tool with which a researcher can quickly determine the value of a particular antioxidant formulation, where increased potency and reduced cost are desired.

It is an object of the present invention to provide a soft gelatin capsule containing natural vitamin E (d-alpha-tocopherol) blended with an additional vitamin E compounds, specifically natural mixed tocopherols (alpha-, beta-, gamma-, delta-) and tocotrienols (alpha-, beta-, gamma-, delta-), to deliver a potent antioxidant vitamin E with superior oxygen radical absorbance capacity (ORAC) value.

It is a further objective of the present invention to enhance the antioxidant capacity of natural vitamin E (d-alpha-tocopherol) for the specific health benefit derived from supplementation with the novel formulation.

It is a further objective of the present invention to provide a more efficacious product to natural vitamin E (d-alpha-tocopherol) product currently available for consumption.

SUMMARY OF THE INVENTION

This invention relates to formulations comprising all forms of natural tocopherols and tocotrienols with enhanced antioxidant activities. These formulations were designed to provide 400 IU, based on one mg d-alpha-tocopherol equals 1.49 IU. The invention further relates to a soft gelatin formulation containing natural vitamin E as d-alpha-tocopherol, mixed tocopherols in the form Alpha, Gamma, Delta, Beta, and tocotrienols, with inseparable tocopherols, in the form of Alpha, Gamma, Delta, Beta. The formulation is contained in a soft gelatin capsule composed of gelatin, glycerin, and water. The formulation is designed to provide antioxidant protection for the cell lipid membrane, and protection against heart disease, cancer, and eye disease.

The antioxidant activities of natural d-alpha-tocopherol, mixed tocopherols and tocotrienols, and formulations comprising all forms of vitamin E were determined employing an improved oxygen radical absorbance capacity (ORAC) assay using fluorescein (FL) as a fluorescent probe, randomly methylated β-cyclodextrin (RMCD) to enhance solubility of lipophilic antioxidants in aqueous medium, 2,2'-azobis (2-amidino-propane) dihydrochloride (AAPH) as peroxyl radical generator, and Trolox as a standard in 75 mM phosphate buffer. The antioxidant activities expressed in μmole Trolox equivalent per gram of d-alpha-tocopherol (87%), mixed tocopherols (70%) and tocotrienols (30%) were found to be 1,293, 1,948 and 1,229; respectively. The data clearly indicate that mixed tocopherols possess higher antioxidant activity than d-alpha-tocopherol.

Vitamin E formulations comprising alpha-, beta-, delta-, and gamma-forms of tocopherols and tocotrienols with enhanced antioxidant activities were developed. All of these formulations provide 400 I.U., based on one mg of d-alpha-tocopherol equals 1.49 I.U. Some of these formulations showed antioxidant activities superior to d-alpha-tocopherol.

This patent discloses formulations comprising all forms of tocopherols and tocotrienols with enhanced antioxidant activities. These formulations provide 400 I.U., based on one mg d-alpha-tocopherol equals 1.49 I.U. Novel formulations of vitamin E comprising a full spectrum of all forms of vitamin E, which possess significantly higher antioxidant activity than alpha-tocopherol are disclosed.

Other features and advantages of the present invention will become more apparent from the following detailed description, which illustrate, by way of example, the principles of the invention.

DETAILED DESCRIPTION OF THE PREFERRED EMBODIMENTS

The antioxidant activity, commonly referred to as oxygen radical absorbance capacity (ORAC), of a lipophilic substance was measured employing a newly developed assay. This assay is based on the use of: (a) fluorescein (FL) as the fluorescent probe, (b) randomly methylated β-cyclodextrin (RMCD) as a molecular host to enhance the solubility of lipophilic antioxidants in aqueous solution, (c) 2,2'-azobis (2-amidino-propane) dihydrochloride (AAPH) as a peroxyl radical generator, and (d) 6-hydroxy-2,5,7,8-tetramethyl-2-carboxylic acid (Trolox) as a standard in 75 mM phosphate buffer (pH 7.4).

The antioxidant activities of vitamin E formulations comprising all compounds of tocopherols and tocotrienols were determined employing an improved oxygen radical absorbance capacity (abbreviated ORACFL-LIPO) assay using fluorescein (FL) as the fluorescent probe, randomly methylated P-cyclodextrin (RMCD) as the water solubility enhancer for lipophilic antioxidants in 75 mM phosphate buffer (pH 7.4).

In the presence of peroxyl radicals derived from AAPH, the indicator FL gradually loses its fluorescence. The antioxidant activity of a substance is measured by its ability to retain the fluorescence of FL in the presence of peroxyl radicals. The net protection of FL was measured as previously described by Ou et al.

Chemicals and Apparatus

Randomly methylated β-cyclodextrin (RMCD) was purchased from Cyclolab R&D Ltd. (Budapest, Hungary). Fluorescein (FL) and 6-hydroxy-2,5,7,8-tetramethyl-2-carboxylic acid (Trolox) were purchased from Aldrich (Milwaukee, Wis.). 2,2'-azobis (2-amidino-propane) dihydrochloride (AAPH) was obtained from Wako Chemicals USA (Richmond, Va.). 87% d-alpha-Tocopherol (containing 13% soy bean oil) and 70% mixed tocopherols (containing 30% soy bean oil) were purchased from Archer Daniels Midland. Each gram of 70% mixed tocopherols contains 114 mg d-alpha-tocopherol, 11 mg d-beta-tocopherol, 457 mg d-gamma-tocopherol, and 131 mg d-delta-tocopherol.

Tocotrienols oil was purchased from Oryza Oil and Fat Chemical Co. in Japan. Tocotrienols oil contains 35% total tocopherols and tocotrienols (12.6% gamma-tocotrienol, 7.2% alpha-tocotrienol, and 12.7% alpha-tocopherol). Palm oil containing 50% total tocopherols and tocotrienols (10% alpha-tocopherol, 11% alpha-tocotrienol, 20% gamma-tocotrienol, and others) was obtained from Carotech (Edison, N.J.).

All other standards were commercially available form Sigma or Aldrich. All ORAC analyses were performed on a COBAS FARA II analyzer (Roche Diagnostic System Inc., Branchburg, N.J.) using an excitation wavelength of 493 nm and an emission filter of 515 nm.

Sample Preparation

Approximately 0.5 g of sample was dissolved in 20 mL of acetone. An aliquot of sample solution was appropriately diluted with 7% RMCD solvent (w/v) made in a 50% acetone-water mixture (v/v) and was shaken for 1 hr at room temperature on an orbital shaker at 400 rpm. The sample solution was ready for analysis after further dilution with 7% RMCD solvent.

Automatic ORAC Assay

The automated ORAC assay was carried out on a COBAS FARA II spectrofluorometer centrifugal analyzer as previously described (9). With the exception of samples and Trolox standards, which were made in 7% RMCD solvent, all other reagents were prepared at 75 mM phosphate buffer (pH 7.4). In the final assay mixture (0.4 mL total volume), FL ($6.3 \times 10^{-8}$ M) was used as a target of free radical attack and AAPH ($1.28 \times 10^{-2}$ M) was used as a peroxyl radical generator. 7% RMCD was used as the blank, and Trolox (12.5, 25, 50, and 100 μM) was used as the control standard. The analyzer was programmed to record the fluorescence of FL every minute after the addition of AAPH. All measurements were expressed relative to the initial reading. Final results were calculated using the differences of areas under the FL decay curves between the blank and a sample. These results were expressed as micromoles Trolox equivalent (TE) per gram, as previously described by Ou et al.

The antioxidant activity, commonly referred to as oxygen radical absorbance capacity (ORAC), of a lipophilic substance was measured employing a newly developed assay. This assay is based on the use of: (a) fluorescein (FL) as the fluorescent probe, (b) randomly methylated P-cyclodextrin (RMCD) as a molecular host to enhance the solubility of lipophilic antioxidants in aqueous solution, (c) 2,2'-azobis (2-amidino-propane) dihydrochloride (AAPH) as a peroxyl radical generator, and (d) 6-hydroxy-2,5,7,8-tetramethyl-2-carboxylic acid (Trolox) as a standard in 75 mM phosphate buffer (pH 7.4).

In the presence of peroxyl radicals derived from AAPH, the indicator FL gradually loses its fluorescence. The antioxidant activity of a substance is measured by its ability to retain the fluorescence of FL in the presence of peroxyl radicals. The net protection of FL was determined as previously described by Ou et al.

The ORAC value was calculated as μmole Trolox equivalent per gram sample (μmole TE/g); one gram of sample has antioxidant activity equals to how many μmole Trolox. The μmole Trolox equivalent per 400 I.U. of the sample is calculated as follows:

μmole TE/400 I.U.=μmole TE/g×total weight in grams of vitamin E formula which gives 400 I.U.

Tables (1) and (2) list the ORAC data expressed in μmole Trolox equivalent (TE) per gram of tested antioxidant sample. The formulations in Table (2) differ from those in Table (1) in that the Table (2) formulations further include Palm Oil and there is a slight modification in the ingredients of Formula 2 in Table (2) as compared to Formula 2 in Table (1). The results of data in Table (1) showed that the synthetic vitamin E acetate showed no antioxidant activity under current experimental conditions, supporting the essential role of the phenolic type hydroxyl for radical trapping antioxidant activity of vitamin E.

The IUs (International Unit) of a sample are based on one mg of alpha-tocopherol equals 1.49 IU.

The following are the percentage of alpha-tocopherol and the corresponding IUs in each ingredient used in the formulations listed in Tables (1) and (2):

(a) Natural vitamin E contains 87% alpha-tocopherol, which means that each gram of natural E contains 870 mg alpha-tocopherol×1.49=1300 IU, i.e. natural vitamin E contains 1300 IU per gram (b) 90% Mixed tocopherols contains 6.8% alpha-tocopherol, which means one gram of 90% mixed tocopherols contains 68 mg alpha-tocopherol×1.49=101 IU, i.e. 90% mixed tocopherols contains 101 IU per gram (c) 70% Mixed tocopherols contains 11.4% alpha-tocopherol, which means one gram of 70% mixed tocopherols contains 114 mg alpha-tocopherol×1.49=170 IU, i.e. 70% mixed tocopherols contains 170 IU per gram (d) 30% Tocotrienols (Oryza) contains 13% alpha-tocopherol, which means one gram of 30% tocotrienols contains 130 mg alpha-tocopherol×1.49=200 IU, i.e. 30% tocotrienols contains 200 IU per gram (e) 50% Tocotrienols (Carotech) contains 10% alpha-tocopherol, which means one gram of 50% tocotrienols contains 10 mg alpha-tocopherol×1.49=150 IU, i.e. 50% tocotrienols contains 150 IU per gram

TABLE 1

Antioxidant activities of vitamin E formulations[f]

| Sample | μmole TE/g | μmole TE/400 IU[g] |
|---|---|---|
| d-alpha-Tocopheral (87%), 1300 IU | 1,293 ± 64 | 398 |
| Tocotrienols (30%) (Oryza), 134 IU | 1,229 ± 20 | |
| Mixed Tocopherols (70%), 120 IU | 1,948 ± 76 | |
| Alpha-Tocopherol Acetate | 14 ± 10 | |
| Formula-1 | 2,036 ± 116 | 1,063 |
| Formula-2 | 1,735 ± 25 | 786 |
| Formula-3 | 1,460 ± 156 | 530 |
| Formula-4 | 1,303 ± 45 | 434 |

Table (1) notes:
[f]The following are the composition of each formula listed in Table (1) which gives 400 IU:
Formula-1: 307 mg alpha-tocopherol (87%), 15 mg tocotrienols (30%), 200 mg mixed tocopherols (70%).

TABLE 1-continued

Antioxidant activities of vitamin E formulations[f]

| Sample | μmole TE/g | μmole TE/400 IU[g] |
|---|---|---|

Formula-2: 293 mg alpha-tocopherol (87%), 10 mg tocotrienols (30%), 150 mg mixed tocopherols (70%).
Formula-3: 303 mg alpha-tocopherol (87%), 10 mg tocotrienols (30%), 50 mg mixed tocopherols (70%).
Formula-4: 316 mg alpha-tocopherol (87%), 16.5 mg tocotrienols (30%).
[g]μmole TE/400 IU = μmole TE/g × total weight in grams of vitamin E formula which gives 400 IU

TABLE 2

Antioxidant activities of vitamin E formulations[h]

| Sample | μmole TE/g | μmole TE/400 IU[i] |
|---|---|---|
| d-alpha-Tocopheral (87%), 1300 IU | 1,293 ± 80 | 413 |
| Tocotrienols (30%, Oryza) | 1,361 ± 88 | |
| Tocopherols (50%, Carotech) | 3,112 ± 232 | |
| Mixed Tocopherols (70%) | 2,256 ± 248 | |
| Mixed Tocopherols (90%) | 2,674 ± 146 | |
| Formula-2 | 1,945 ± 113 | 881 |
| Formula-2a | 1,857 ± 60 | 860 |
| Formula-2ab | 1,825 ± 120 | 872 |
| Formula-2ac | 1,828 ± 90 | 837 |

Table (2) Notes:
[h]The following are the composition of each formula listed in Table (2) which gives 400 IU:
Formula-2: 293 mg alpha-tocopherol (87%), 10 mg tocotrienols (30%), 150 mg mixed tocopherols (70%).
Formula-2a: 293 mg alpha-tocopherol (87%), 10 mg tocotrienols (30%), 160 mg mixed tocopherols (70%).
Formula-2ab: 293 mg alpha-tocopherol (87%), 10 mg tocotrienols (30%), 175 mg mixed tocopherols (70%).
Formula-2ac: 293.5 mg alpha-tocopherol (87%), 4.3 mg tocotrienols (50%), 160 mg mixed tocopherols (70%).
[i]μmole TE/400 IU = μmole TE/g × total weight in grams of vitamin E formula which gives 400 IU Data in table (1) revealed that alpha-tocopherol (87%) had a value of 1,293 μmole Trolox equivalent (TE) per gram, from this data one can calculate the μmole TE of 400 I.U. of alpha-tocopherol (87%) to be 398 (307.7 mg alpha-tocopherol is equivalent to 400 I.U.). Similarly, the μmole TE per 400 I.U. of each vitamin E formula can be calculated, and the results are given in table (1). As can be seen from data in table (1), the antioxidant activities of natural vitamin E formulae 1, 2 and 3 are higher than that of natural d-alpha-tocopherol (87%) at its specific concentration in the specified formula. Similar relative antioxidant activities were also obtained with tocotrienols from either Palm Oil or Oryza Oil as shown by the formulations in Table (2). These results indicate that the various isomers of natural tocopherols and tocotrienols could enhance the antioxidant activity of natural vitamin E (d-alpha-tocopherol). A recent study showed that a combination of alpha-, gamma-, and delta-tocopherols in a concentration found in nature is more potent than alpha-, gamma-, and delta-tocopherol alone in enhancing nitric oxide release, and inhibiting human platelet aggregation and lipid peroxidation.

The biological activity of vitamin E has generally been associated with its well-defined antioxidant property, specifically against lipid peroxidation in biological membranes. Therefore, it is anticipated that enhancing the antioxidant property of vitamin E as well as the full spectrum of various vitamin E forms might provide better health benefits than just alpha-tocopherol.

The antioxidant activities of alpha-tocopherol, mixed tocopherol and tocotrienols, and vitamin E formulations comprising all forms of tocopherols and tocotrienols were determined employing an oxygen radical absorbance capacity assay suitable for lipophilic antioxidants. The results of this study clearly indicate that mixed tocopherols possess higher antioxidant activity than d-alpha-tocopherol.

Vitamin E formulations, providing 400 I.U., comprising various forms of tocopherols and tocotrienols with enhanced antioxidant activities were developed. Some of these formulations showed antioxidant activities superior to d-alpha-tocopherol.

Formula-1 and Formula-2 were found to possess a much higher ORAC value than that of natural vitamin E (d-alpha-tocopherol). Formula-3 also showed an increase (25%) in its antioxidant activity as compared to alpha-tocopherol. Formula-4 showed slightly higher antioxidant activity that alpha-tocopherol. Formulae-1, -2, -3 contain alpha-tocopherol, mixed-tocopherols and tocotrienols, whereas Formula-4 contains only alpha-tocopherol and tocotrienols. As mentioned above, mixed tocopherols provide additional health benefits, therefore, Formula-1 or Formula-2 would be recommended since they contain all natural mixed tocopherols and tocotrienols and possess significantly higher antioxidant activity than alpha-tocopherol, and their cost is comparable to the widely marketed natural d-alpha-tocopherol. Each gram of 70% mixed tocopherols contains 114 mg d-alpha-tocopherol, 11 mg d-beta-tocopherol, 457 mg d-gamma-tocopherol, and 131 mg d-delta-tocopherol. From these data, the amount of gamma-tocopherol in Formula-1 and Formula-2 is calculated to be 24% and 21%; respectively. These values are in accordance with the recommended amounts of gamma-tocopherol in vitamin B supplement. This study was published in Proceedings of the national Academy of Science, USA (1997), and suggested that vitamin E supplement should have at least 20% gamma-tocopherol. Formula-3, on the other hand, contains only 9% gamma-tocopherol.

In one preferred embodiment, the invention comprises a composition of natural vitamin E with enhanced antioxidant activity, comprising: (a) 55 to 85% by weight of d-alpha-tocopherol; (b) 10 to 40% by weight of mixed tocopherols; and (c) 2 to 3% by weight of tocotrienols. In another embodiment, the mixed tocopherols comprise 70% tocopherols in the amounts of 5 to 15% alpha-tocopherol, 1 to 3% beta-tocopherol, 30 to 50% gamma-tocopherol, and 10 to 20% delta-tocopherol. In another embodiment, the mixed tocopherols comprise 90% tocopherols in the amounts of 10 to 20% alpha-tocopherol, 2 to 4% beta-tocopherol, 50 to 80% gamma-tocopherol, and 10 to 20% delta-tocopherol. In another embodiment, the tocotrienols are obtained from rice oil and said tocotrienols contain 10 to 15% alpha-tocopherol, 10 to 12% alpha-tocotrienol, 10 to 12% gamma-tocotrienol, and 2 to 10% other tocopherols and tocotrienols. In another embodiment, the tocotrienols are obtained from palm oil and said tocotrienols contain 8 to 14% alpha-tocopherol, 8 to 14% alpha-tocotrienol, 15 to 30% gamma-tocotrienol, and 5 to 10% delta-tocotrienol.

What is claimed is:

1. A method of maintaining cardiovascular health comprising the step of providing to a subject, a composition comprising about 55 to about 85% by weight of d-alpha-tocopherol, about 10 to about 40% by weight of mixed tocopherols comprising alpha-tocopherol, beta-tocopherol, delta-tocopherol, and gamma-tocopherol; and about 1 to about 3% by weight of tocotrienols oil.

2. The method of claim 1, wherein said mixed tocopherols comprise 70% tocopherols in the amounts of 5 to 15% alpha-tocopherol, 1 to 3% beta-tocopherols, 30 to 50% gamma-tocopherol, and 10 to 20% delta-tocopherol.

3. The method of claim 1, wherein said mixed tocopherols comprise 90% tocopherols in the amounts of 10 to 20% alpha-tocopherol, 2 to 4% beta-tocopherol, 50 to 80% gamma-tocopherol, and 10 to 20% delta-tocopherol.

4. The method of claim 1, wherein said tocotrienols oil comprises rice oil, said rice oil comprising 10 to 15% alpha-tocopherol, 10 to 12% alpha-tocotrienol, 10 to 12% gamma-tocotrienol, and 2 to 10% other tocopherols and tocotrienols.

5. The method of claim 1, wherein said tocotrienols oil comprises palm oil, said palm oil comprising 8 to 14% alpha-tocopherol, 8 to 14% alpha-tocotrienol, 15 to 30% gamma-tocotrienol, and 5 to 10% delta-tocotrienol.

\* \* \* \* \*